United States Patent [19]

Wieringa

[11] 4,374,133
[45] Feb. 15, 1983

[54] TRICYCLIC COMPOUNDS

[75] Inventor: Johannes H. Wieringa, Heesch, Netherlands

[73] Assignee: Akzo n.v., Oss, Netherlands

[21] Appl. No.: 331,303

[22] Filed: Dec. 16, 1981

[30] Foreign Application Priority Data

Dec. 22, 1980 [NL] Netherlands .................. 8006955

[51] Int. Cl.³ .................. A61K 31/395; C07D 245/04; C07D 267/00; C07D 281/00
[52] U.S. Cl. .................. 424/244; 260/239 DD; 260/330; 260/330.7; 424/275
[58] Field of Search .......... 260/239 DD, 330, 330.7; 424/244, 275

[56] References Cited

U.S. PATENT DOCUMENTS 3,452,046  6/1969  Yale et al. ................. 260/327
3,497,499  2/1970  Houlihan et al. ........ 260/239 DD
3,803,143  4/1974  Tanaka et al. ............ 260/330 X

FOREIGN PATENT DOCUMENTS 2128097 10/1972 France.

Primary Examiner—Richard Raymond
Attorney, Agent, or Firm—Abelman, Frayne & Rezac

[57] ABSTRACT

The present invention relates to new dibenzoxazonine, dibenz-oxazecine or dibenzo-oxaazacycloundecane derivatives and corresponding thia- and aza derivatives thereof, of the general formula I:

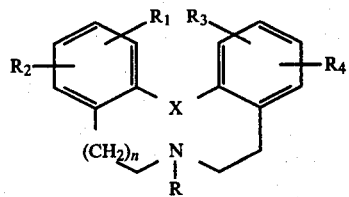

or a pharmaceutically acceptable acid addition salt or nitrogen oxide thereof, in which
  X represents oxygen, sulphur or the group $NR_5$,
  $R_5$ is hydrogen or alkyl (1–4 C),
  $R_1$, $R_2$, $R_3$, $R_4$ each represent hydrogen, hydroxy, halogen, cyano, alkyl, alkoxy, aralkoxy, alkylthio, methylenedioxy, $CF_3$, $NO_2$, $NH_2$, hydroxyalkyl or an acyloxy group,
  R represents hydrogen, alkyl, alkenyl or aralkyl, hydroxyalkyl or acyloxyalkyl and
  n represents the number 0, 1 or 2, having valuable C.N.S. properties.

4 Claims, No Drawings

TRICYCLIC COMPOUNDS

The present invention relates to new dibenz-oxazonine, dibenz-oxazecine or dibenzo-oxaazacycloundecane derivatives and corresponding thia- and aza derivatives thereof, to processes for their preparation and to pharmaceutical preparations containing same.

In particular the invention relates to compounds having the general formula I:

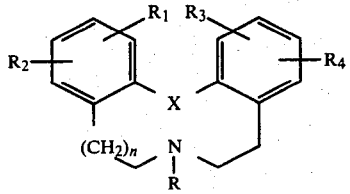

or a pharmaceutically acceptable acid addition salt or nitrogen oxide thereof, in which X represents oxygen, sulphur or the group $NR_5$,
$R_5$ is hydrogen or alkyl (1-4 C),
$R_1$, $R_2$, $R_3$, $R_4$ each represent hydrogen, hydroxy, halogen, cyano, alkyl, alkoxy, aralkoxy, alkylthio, methylenedioxy, $CF_3$, $NO_2$, $NH_2$, hydroxyalkyl or an acyloxy group,
R represents hydrogen, alkyl, alkenyl or aralkyl, hydroxyalkyl or acyloxyalkyl and
n represents the number 0, 1 or 2.

The compounds in accordance with the invention are valuable C.N.S. (central nervous system) active compounds, and in particular the compounds in question possess strong anti-psychotic properties.

The compounds I are manufactured in a manner commonly used for such compounds. A suitable method consists of the ring closure of a compound having the formula II:

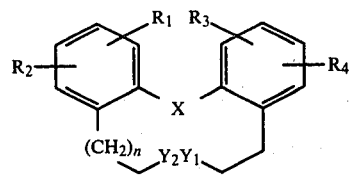

in which X, $R_1$, $R_2$, $R_3$, $R_4$ and n have the meanings assigned above and $Y_1$ and $Y_2$ represent either both a "leaving" group or both an oxo (aldehyde) group or one represents a "leaving" group and the other represents the group —NHR, whereby R has the meaning already indicated above.

If both $Y_1$ and $Y_2$ represent a leaving group, such as halogen or a sulphonyloxy group, ring closure resulting in a compound of formula I takes place by condensation with ammonia or the amine (III): $H_2NR$, whereby R has the meanings assigned above. If both $Y_1$ and $Y_2$ represent an oxo group, the desired product is obtained by reaction with the said amine $H_2NR$ in the presence of a reducing agent such as $LiAlH_4$, di-isobutylaluminiumhydride or $NaBH_4$.

A second method currently employed consists of the reduction of a compound having the general formula IV:

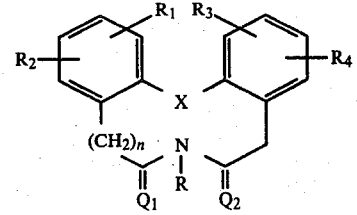

where X, $R_1$, $R_2$, $R_3$, $R_4$ and n have the meanings already specified above and $Q_1$ and $Q_2$ represent hydrogen (2H) or oxygen, with the proviso that at least one of the groups $Q_1$ and $Q_2$ represents oxygen.

This reduction takes place in the manner conventionally employed for the reduction of an amide, preferably with the aid of a complex metal hydride such as lithium aluminumhydride, or with diborane or with boronhydride in dimethylsulphide and tetrahydrofuran.

The compounds of the formulae II and IV used as starting products are manufactured in a manner commonly used for the preparation of such compounds. For the sake of completeness reference is made to pages 15/16 in which a number of currently employed methods of manufacture are shown in schematic form.

It is obviously possible to convert a compound of the invention into another compound of the invention after having carried out one of the aforesaid methods of preparation.

Thus for example the unsubstituted (at the nitrogen atom) amine in accordance with formula I (R=H) can be alkylated in the usual manner, e.g. by reaction with an alkyl, alkenyl or aralkyl halide or by acylating the relevant nitrogen atom and subsequently reducing the N-acyl compound thus formed. The introduction of a methyl group to the nitrogen atom is preferably carried out through an Eschweiler-Clarke reaction (reaction with formaldehyde and formic acid) or through a reaction with formaldehyde and sodiumcyanoborohydride in a suitable solvent, e.g. acetonitrile.

Another usual method consists of converting the amine I which is substituted at the nitrogen atom (R=aralkyl, alkenyl or alkyl) into the corresponding unsubstituted amine (R=H) by means of a de-(ar)alkylation. Thus a >N-benzyl group can be converted by catalytic hydrogenation in a simple manner into the corresponding >NH group. Another possibility of de-(ar)alkylation comprises the reaction of the (ar)alkyl or alkenyl substituted amine of formula I with an ester of chloroformic acid or with BrCN, followed by hydrolysis of the resultant carbamate. Moreover the carbamate obtained may also be converted into a methyl group by a conventional reduction method.

A conventional hydrolysis of an alkoxy substituent—and preferably a methoxy substituent—at the phenyl group(s) into the corresponding hydroxy group, e.g. with the aid of an acid such as $BBr_3$ or HBr, may be carried out to obtain compounds of formula I, in which at least one of the symbols $R_1$, $R_2$, $R_3$ or $R_4$ is hydroxy.

If one of the symbols $R_1$-$R_4$ represents a benzyloxy group it may be converted into the corresponding hydroxy group by a conventional reduction.

Furthermore a nitro group ($NO_2$) at one or both phenyl moieties can be reduced in a conventional manner into an amino group. In its turn this amino moiety can be converted into a cyano moiety by diazotization and subsequent reaction with CuCN.

A cyano (CN) moiety at one or both phenyl moieties can be hydrolysed and subsequently be reduced to obtain the corresponding hydroxymethyl group.

A hydroxy group in the definition of $R_1$-$R_4$ or the hydroxy group of the hydroxy-alkyl moiety in the definition of R can be converted into the corresponding acyloxy group by reaction with the desired carboxylic acid or with an acid halide, anhydride or reactive ester thereof.

The acid addition salts of the compounds in accordance with the invention are manufactured in the usual manner by reacting the free base I with an acid, such as HCl, HBr or HI, phosphoric acid, acetic acid, maleic acid, malonic acid, fumaric acid, succinic acid, tartaric acid, citric acid, ascorbic acid or salicylic acid.

The nitrogen oxides I are obtained by oxidation of the nitrogen atom by means of peracids, $H_2O_2$ or oxidising metaloxides, such as $MnO_2$.

The compounds I can be administered either enterally or parenterally. Mixed with suitable carriers they can be processed into a form which is suitable for oral administration such as pills, tablets and coated tablets. For injection purposes the compounds of formula I are dissolved, emulsified or suspended in a liquid suitable for injection. The compounds I can furthermore be compounded in the form of a suppository or spray.

The instant compounds are preferably used in a daily dosage of 0.01 mg up to 10 mg per kilogram body weight. For human use a daily dosage between 1 and 500 mg is recommended.

By an alkyl group in the definition of $R_1$, $R_2$, $R_3$ and $R_4$ is meant a saturated alkyl group with 1 to 6 carbon and preferably 1-4 carbon atoms, such as methyl, ethyl, propyl, isopropyl, butyl, isobutyl, tert. butyl, pentyl and hexyl.

An alkyl group in the definition of R has the same meanings but in addition may also be a cycloalkyl or cycloalkyl-alkyl group with 3-6 carbon atoms, such as cyclohexyl, cyclopentyl, cyclobutylmethyl and cyclopropylmethyl.

By an alkenyl group in the definition of R is to be understood an unsaturated alkyl group with 2 up to 6 carbon atoms and preferably 3 or 4 carbon atoms such as allyl and 2-butenyl.

By an aralkyl group in the definition of R is meant an alkyl group (as defined above for $R_1$, $R_2$, $R_3$ and $R_4$) which is substituted with an aromatic group such as a phenyl or naphthyl group. The said aromatic group can be substituted with one or more alkyl (1-4 C), halogen, hydroxy or alkoxy groups. Preferably a substituted or unsubstituted phenylalkyl group is meant having 7-12 carbon atoms, such as phenylmethyl, phenylethyl, m.p. dihydroxyphenylethyl, m.p. dimethoxyphenylethyl and phenylpropyl.

The alkyl moiety which is present in the "hydroxyalkyl" "alkylthio" and "alkoxy" groups (see definition of $R_1$, $R_2$, $R_3$ and $R_4$) has the same meaning as is defined for "alkyl" in the definition of $R_1$-$R_4$.

The alkyl moiety present in the "hydroxyalkyl" and "acyloxyalkyl" groups (see definition of R) has the same meaning as is defined for the alkyl group in the definition of R.

The acyloxy group in the definition of $R_1$-$R_4$ is derived from a carboxylic acid with 1-18 carbon atoms especially from an aliphatic or phenyl-aliphatic carboxylic acid, such as acetic acid, propionic acid, butyric acid, valeric acid, phenylacetic acid, and phenylpropionic acid. More particularly preference is given to acyloxy groups with a "longer" aliphatic or phenyl-aliphatic chain. Preference is given especially to acyloxy groups with 8 to 18 carbon atoms such as octanoyloxy, decanoyloxy, lauroyloxy, myristoyloxy, palmitoyloxy, stearoyloxy, and cinnamoyloxy. The acyloxy component of the acyloxyalkyl group (definition R) has the same meaning.

By "halogen" in the definition of $R_1$-$R_4$ is to be understood: fluorine, chlorine, bromine or iodine; chlorine is to be preferred.

In the Examples the following numbering and nomenclature have been used:

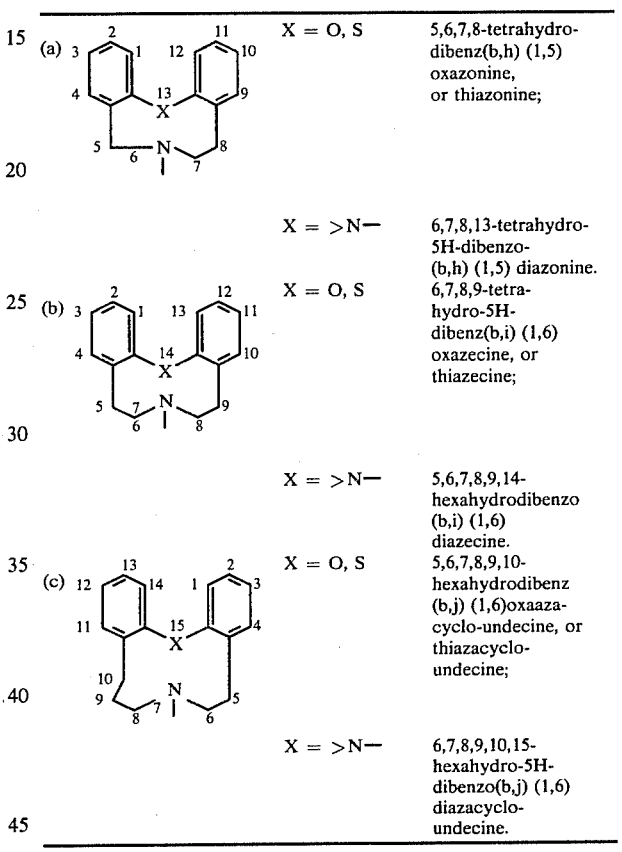

(a) X = O, S — 5,6,7,8-tetrahydro-dibenz(b,h) (1,5) oxazonine, or thiazonine;

X = >N— 6,7,8,13-tetrahydro-5H-dibenzo-(b,h) (1,5) diazonine.

(b) X = O, S — 6,7,8,9-tetrahydro-5H-dibenz(b,i) (1,6) oxazecine, or thiazecine;

X = >N— 5,6,7,8,9,14-hexahydrodibenzo(b,i) (1,6) diazecine.

(c) X = O, S — 5,6,7,8,9,10-hexahydrodibenz(b,j) (1,6)oxaazacyclo-undecine, or thiazacyclo-undecine;

X = >N— 6,7,8,9,10,15-hexahydro-5H-dibenzo(b,j) (1,6) diazacyclo-undecine.

Preferred compounds of the invention are those compounds of formula I in which (whether or not in combination)
X represents oxygen,
n has the value 1,
R represents alkyl (1-4 C) and is preferably methyl, and either both phenyl groups are unsubstituted or one or both phenyl groups are mono-substituted.

EXAMPLE 1

7-benzyl-6,7,8,9-tetrahydro-5H-dibenz-(b,i)(1,6)oxazecine a. Under nitrogen a solution of 12 g 2,2'-oxybisbenzeneacetic acid in 300 ml of dry tetrahydrofuran (THF) was added while stirring to a suspension of 12 g LiAlH$_4$ in 750 ml of dry ether. After this addition the mixture was refluxed for about one hour, whereupon 48 ml of water was added dropwise, while cooling the mixture on ice.

The white inorganic precipitate formed was subsequently removed and washed with THF.

The filtrate was evaporated to dryness resulting in an oily residue.

Yield: 10.7 g.

Rf in toluene:ethylacetate (1:1)=0.45 on SiO$_2$.

b. A mixture of 5.5 g 2,2'-oxybisbenzene-ethanol from a. and 100 ml 48% hydrogen bromide was heated whilst being strongly agitated for 4 hours to 130° C. After cooling the reaction mixture, it was poured into 500 ml water and the resulting mixture extracted with ether. The ether extract was washed with water, dried and evaporated under vacuum.

The residue was then purified over a silicagel column. Yield: 5.7 g (oil).

Rf in hexane:toluene (8:2)=0.50 on SiO$_2$.

c. A mixture of 9.7 g 1,1'-oxybis(2-($\beta$-bromoethyl)-benzene) from b. and 13 ml benzylamine dissolved in 970 ml dry xylene was refluxed for 16 hours.

After cooling the mixture 1 n NaOH was added, the organic layer was separated and subsequently evaporated to dryness. The residue was purified over a silicagel column.

Yield: 6.25 g (oil).

Rf in methanol:acetone (9:1)=0.75 on SiO$_2$.

EXAMPLE 2

6,7,8,9-tetrahydro-5H-dibenz(b,i)(1,6)oxazecine 6,5 g 7-benzyl-6,7,8,9-tetrahydro-5H-dibenz(b,i)(1,6)oxazecine was dissolved in 450 ml glacial acetic acid. 1 g of Pd/C (10%) was added to this solution after which hydrogen was introduced in the reaction mixture for two hours. The catalyst was then removed and the filtrate evaporated in vacuo. The residue was dissolved in dilute ammonia and the mixture extracted with ether. The ether extract was washed, dried and evaporated.

Yield 4.3 g (oil), melting point HCl salt: 246° C. Rf in methanol:acetone (9:1)=0.10 on SiO$_2$.

EXAMPLE 3

(a)
6,7,8,9-tetrahydro-7-methyl-5H-dibenz(b,i)(1,6)oxazecine 1 gram of 6,7,8,9-tetrahydro-5H-dibenz(b,i)(1,6)oxazecine was mixed with 4 ml formic acid and 3.8 ml of 37% formalin. This mixture was heated for 1 hour at 100° C. After cooling 0.5 ml of concentrated hydrochloric acid was added and the reaction mixture was evaporated. The residue was then dissolved in dilute NaOH, and the mixture extracted with ether. The ether extract was washed, dried and evaporated to dryness.

Yield: 1.05 g (oil).

Rf in methanol:acetone (9:1)=0.25 on SiO$_2$.

(b)
6,7,8,9-tetrahydro-7-methyl-5H-dibenz(b,i)(1,6)oxazecine (Z)-2-butene dioate (1:1)

1.05 g 6,7,8,9-tetrahydro-7-methyl-5H-dibenz(b,i)(1,6)oxazecine was dissolved in 6 ml ethanol. A solution of 0.6 g maleic acid in 3 ml ethanol was added to this solution. The crystals formed were removed and subsequently washed with ether.

Yield: 1.3 g; melting point 158° C.

EXAMPLE 4

In a similar manner to that described in Examples 1, 2 and 3 the following compounds were produced:
3-chloro-6,7,8,9-tetrahydro-5H-dibenz(b,i)(1,6)oxazecine.HCl, m.p. 156° C.;
3-chloro-6,7,8,9-tetrahydro-7-methyl-5H-dibenz(b,i)(1,6)oxazecine, m.p. maleate salt: 145° C.;
6,7,8,9-tetrahydro-3,7-dimethyl-5H-dibenz(b,i)(1,6)oxazecine, m.p. maleate salt: 165° C.;
6,7,8,9-tetrahydro-7-methyl-1,2-dimethoxy-5H-dibenz(b,i)(1,6)oxazecine;
5,6,7,8,9,14-hexahydro-7-benzyl-14-methyldibenzo(b,i)(1,6)diazecine, Rf in toluene:ethanol (8:2)=0,38 on SiO$_2$;
6,7,8,9-tetrahydro-7-methyl-5H-dibenzo(b,i)(1,6)thiazecine, m.p. maleate salt: 176° C.;
5,6,7,8,9,10-hexahydro-7-methyldibenzo(b,i)(1,6)oxaazacycloundecine.HCl, m.p. 216° C.;
5,6,7,8,9,10-hexahydro-dibenzo(b,j)(1,6)oxaazacycloundecine.HCl, m.p. 249° C.;
3-chloro-6,7,8,9-tetrahydro-7-cyclopropylmethyl-5H-dibenz(b,i)(1,6)oxazecine.HCl, m.p. 225°–226° C.;
3-chloro-6,7,8,9-tetrahydro-7-benzyl-5H-dibenzo(b,i)(1,6)thiazecine,
Rf in toluene:ethylacetate (8:2)=0,81 on SiO$_2$;
3-chloro-6,7,8,9-tetrahydro-7-methyl-5H-dibenzo(b,i)(1,6)thiazecine, m.p. maleate salt: 182° C.;
2-methoxy-6,7,8,9-tetrahydro-7-benzyl-5H-dibenz(b,i)(1,6)oxazecine, Rf in toluene:ethanol (8:2)=0,61 on SiO$_2$;
2-methoxy-6,7,8,9-tetrahydro-7-methyl-5H-dibenz(b,i)(1,6)oxazecine, Rf in toluene:ethanol (8:2)=0,34 on SiO$_2$;
3-nitro-6,7,8,9-tetrahydro-7-methyl-5H-dibenz(b,i)(1,6)oxazecine;
3-amino-6,7,8,9-tetrahydro-7-methyl-5H-dibenz(b,i)(1,6)oxazecine;
5,6,7,8-tetrahydro-6-methyl-dibenzo(b,h)(1,5)thiazonine.HCl, m.p. 245° C.;
5,6,7,8-tetrahydro-6-methyl-dibenz(b,h)(1,5)oxazonine.HCl, m.p. 235° C.;
1,2-methylenedioxy-6,7,8,9-tetrahydro-7-methyl-5H-dibenz(b,i)(1,6)oxazecine.

EXAMPLE 5

5,6,7,8-tetrahydro-6-methyldibenz(b,h)(1,5)oxazonine (a) A mixture of 8.5 g 2-(2'-hydroxymethylphenoxy)-benzene-ethanol and 40 ml 48% of hydrogen bromide was heated at its boiling point for 6 hours whilst being vigorously stirred. After cooling the mixture, it was diluted with 200 ml water and extracted with ethylacetate. The extract was washed with water, dried over Na$_2$SO$_4$ and evaporated in vacuo. The residue was purified over a silicagel column.

Yield: 4.0 g (oil).

Rf in toluene=0.85 on silicagel.

(b) A solution of 100 ml 22% methylamine in ethanol was added dropwise to a solution of 4 g 1-(2'-bromomethylphenoxy)-2-($\beta$-bromoethyl)benzene (from (a) above) in 30 ml dimethylsulphoxide and 100 ml ethanol 96%, while being vigorously stirred.

The mixture was then poured into 500 ml water and extracted with ether. The ether extract was dried and evaporated in vacuo at 20° C.

Yield: 2.5 g (oil).

Rf in methanol:acetone (9:1)=0.3 on silicagel.

(c) 2.5 g 2-(2'-($\beta$-bromoethyl)phenoxy)-N-methyl-benzenemethanamine obtained from (b) was dissolved in a mixture of 50 ml THF and 100 ml ether and refluxed for 2×24 hours. After cooling it was evaporated and the resultant residue was purified over a silicagel column.

Yield: 0.2 g (oil); melting point HCl salt: 233°–235° C.
Rf in methanol:acetone (9:1)=0.6 on SiO$_2$.

EXAMPLE 6

5,6,7,8,9,10-hexahydro-7-methyl dibenz(b,j)(1,6)oxaazacycloundecine 1,34 g (3,3 mmol.) 1-(2'-(β-bromoethyl)phenoxy)-2-(γ-bromopropyl)benzene in 20 ml EtOH and 20 ml dry D.M.S.O. was introduced in an ampoule. One ml triethylamine and 0.64 g 16.3% by weight of methylamine in D.M.S.O. was then added. The ampoule was sealed and subsequently heated in an oil bath at 80° C. for 4 hours. The reaction mixture was then poured into water and extracted with ether. The ether extract was then washed with dilute HCl. Subsequently the water layer was rendered alkaline and again extracted with ether, whereupon the ether layers collected were washed with water, dried and evaporated. The yield was 410 mg (oil); Rf in methanol:acetone (9:1)=0.25 on SiO$_2$. Melting point HCl salt: 215°–216° C.

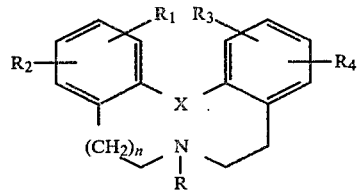

or a pharmaceutically acceptable acid addition salt or nitrogen oxide thereof, in which X represents oxygen, sulphur or the group NR$_5$,
R$_5$ is hydrogen or alkyl (1–4 C),
R$_1$, R$_2$, R$_3$, R$_4$ each represent hydrogen, hydroxy, halogen, cyano, alkyl, alkoxy, aralkoxy, alkylthio, methylenedioxy, CF$_3$, NO$_2$, NH$_2$, hydroxyalkyl, or an acyloxy group,
R represents hydrogen, alkyl, alkenyl or aralkyl, hydroxyalkyl or acyloxyalkyl and
n represents the number 0, 1 or 2.

Reaction Scheme

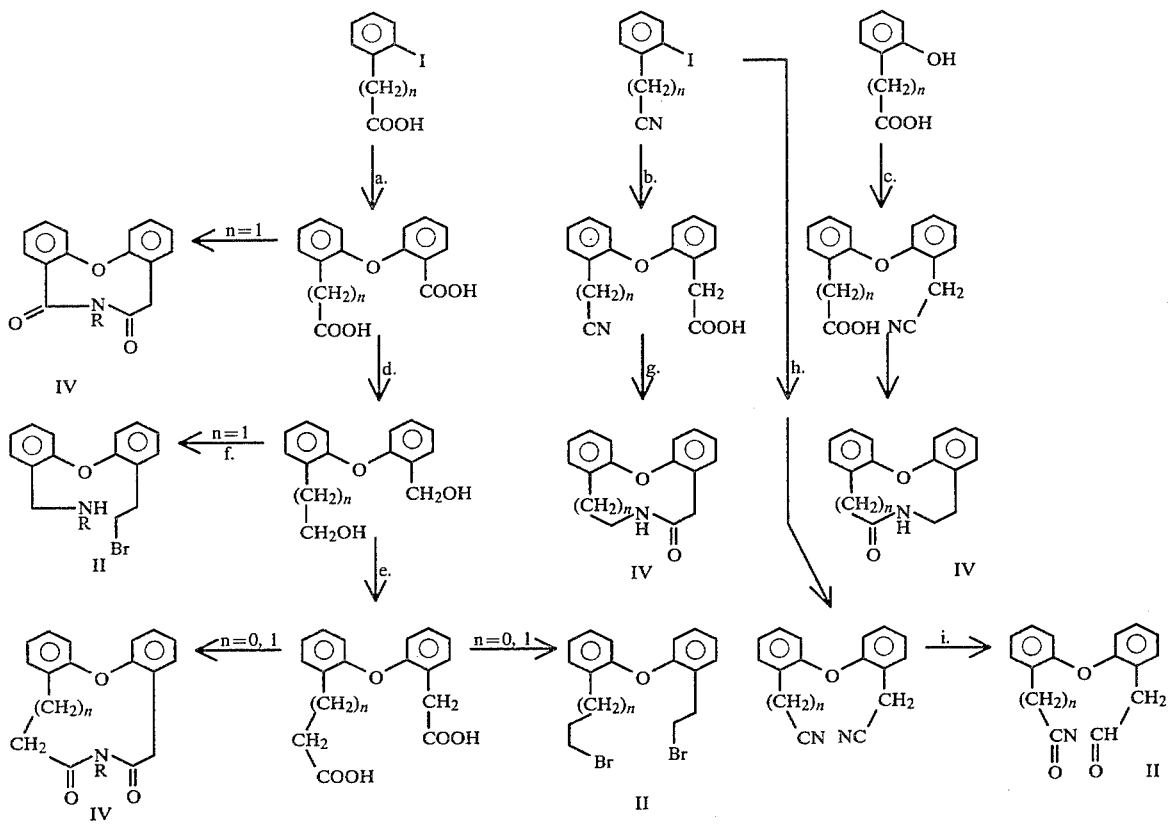

Legend to reaction scheme
a. Reaction with salicylic acid.
b. Reaction with o-hydroxy phenyl acetic acid.
c. Reaction with o-iodine phenylacetonitrile.
d. Reaction with LiAlH$_4$.
e. Reaction with HBr, followed by reaction of the bromide with KCN, after which the nitrile is hydrolysed.
f. Reaction with HBr, followed by reaction of the bromide with 1 eq. RNH$_2$.
g. Reduction with hydrogen and Pd/C followed by ring closure.
h. Reaction with O—hydroxyphenylacetonitrile.
i. Reduction with di-isobutylaluminiumhydride (DIBAH).

I claim:
1. Compound of the general formula I:
2. Compound according to claim 1 having the formula indicated in claim 1, in which wherein in combination:
X represents oxygen, n has the value 1 and
R represents C$_1$–C$_4$ alkyl.
3. A compound according to claim 2 wherein X is oxygen, n=1 and R is methyl.
4. A pharmaceutical composition which contains, as its active ingredient, a pharmaceutically effective amount of a compound according to claim 1 or its acid addition salt or nitrogen oxide derivative thereof in the presence of a pharmaceutically acceptable carrier.

* * * * *